United States Patent [19]
Tanaka

[11] Patent Number: 4,979,923
[45] Date of Patent: Dec. 25, 1990

[54] STUFFED TOY WITH HEATER AND PHASE CHANGING HEAT STORAGE

[75] Inventor: Toshio Tanaka, Yokohama, Japan

[73] Assignee: Sakura Sogyo Co., Ltd., Kawaaki, Japan

[21] Appl. No.: 453,778

[22] Filed: Dec. 20, 1989

Related U.S. Application Data

[63] Continuation-in-part of Ser. No. 304,871, Jan. 30, 1989, abandoned, which is a continuation-in-part of Ser. No. 196,008, May 9, 1988, abandoned.

[51] Int. Cl.⁵ .......... A63H 3/00; A63H 3/52; F24H 7/00; H05B 1/00
[52] U.S. Cl. .......... 446/72; 446/267; 446/295; 219/201; 392/339
[58] Field of Search .......... 219/200, 201, 378, 430, 219/439, 462; 446/14, 71, 72, 73, 74, 76, 227, 267, 295, 296, 472, 484, 369, 370

[56] References Cited

U.S. PATENT DOCUMENTS

| | | | |
|---|---|---|---|
| 1,558,278 | 10/1925 | Phillips | 219/200 X |
| 2,647,125 | 7/1953 | Broyles | 446/72 X |
| 2,774,184 | 12/1956 | Hefferan et al. | 219/200 X |
| 3,293,409 | 12/1966 | Snelling | 219/378 |
| 3,356,828 | 12/1967 | Furness | 219/378 X |
| 3,876,859 | 4/1975 | Franz et al. | 219/439 X |
| 4,204,110 | 5/1980 | Smit et al. | 219/201 X |
| 4,400,287 | 8/1983 | Kimura et al. | 252/70 |
| 4,694,829 | 9/1987 | Frye | 219/200 X |
| 4,714,445 | 12/1987 | Templeton | 446/74 |
| 4,816,000 | 3/1989 | Hsu | 446/74 |

Primary Examiner—Robert A. Hafer
Assistant Examiner—D. Neal Muir
Attorney, Agent, or Firm—Rosen, Dainow & Jacobs

[57] ABSTRACT

A stuffed toy with a heater is disclosed, which comprises a cover configured to resemble a predetermined object and a latent heat storage material disposed in the stuffing in the cover. When the latent heat storage material is heated it undergoes a transition from the solid phase to the liquid phase and stores a heat of dissolution. When it undergoes transition from the liquid phase to the solid phase, it gives off heat so as to maintain the temperature of the toy relatively constant for long periods of time.

27 Claims, 4 Drawing Sheets

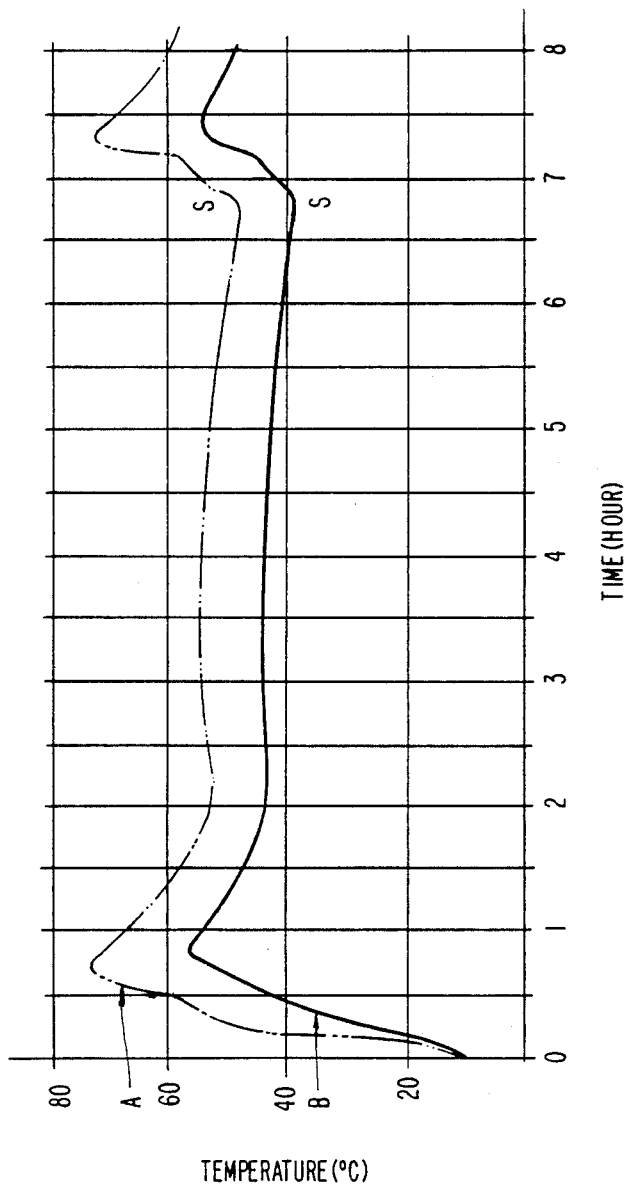

STUFFED TOY WITH HEATER AND PHASE CHANGING HEAT STORAGE

BACKGROUND OF THE INVENTION

This application is a continuation-in-part of application Ser. No. 304,871 filed Jan. 30, 1989, now abandoned, which is a continuation-in-part of application Ser. No. 196,008, filed May 9, 1988 now abandoned.

This invention relates to a stuffed toy with heater, which can heat the body so that an infant or the like may sleep by embracing it in winter seasons or in a cooled room.

There is a well-known stuffed animal toy or the like, which is heated substantially to the same temperature of an animal by a heater, which uses a dry cell for heat generation and is accommodated in a wadding of stuffing so that the toy can give a sense of an actual animal or can be used as a heater in winter seasons or the like.

In the stuffed toy as noted above, an electric resistance heater is energized for heating from a battery. Therefore, while the battery is new, it provides high voltage so that high temperature can be obtained. As the battery is consumed, however, the temperature is reduced initially gradually and eventually suddenly.

Further, the temperature is changed in dependence on the heat insulation effect of a heat insulator or ambient temperature and independently of the capacity of the battery.

When an infant is sleeping with a toy embraced, the heat radiation varies depending on how the toy is embraced and whether he or she is under a coverlet.

SUMMARY OF THE INVENTION

This invention has been devised in order to solve the above problems. According to the invention, a latent heat storage material is accommodated in a heat insulation member covered by a cover.

When the latent heat storage material is heated, it undergoes a transition from the solid phase to the liquid phase. At this time, it stores heat according to the heat of its dissolution.

In use, when the latent heat storage material is cooled so as to be solidified, it gives off a heat of solidification. Thus, the heat is dissipated so as to maintain a constant temperature for a long time. The stuffed toy thus can be given a feeling resembling that of an actual animal or human body.

BRIEF DESCRIPTION OF THE DRAWINGS

FIG. 7 is a graph showing temperature characteristics of a stuffed toy according to the invention which uses a heat storage material disclosed by Kimura et al., U.S. Pat. No. 4,400,287 as the latent heat storage material.

DETAILED DESCRIPTION OF THE INVENTION

Figure 1:
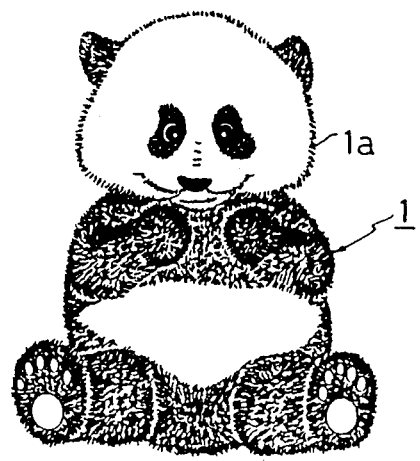
FIG. 1 is a front view showing an embodiment of the invention.
Figure 2:
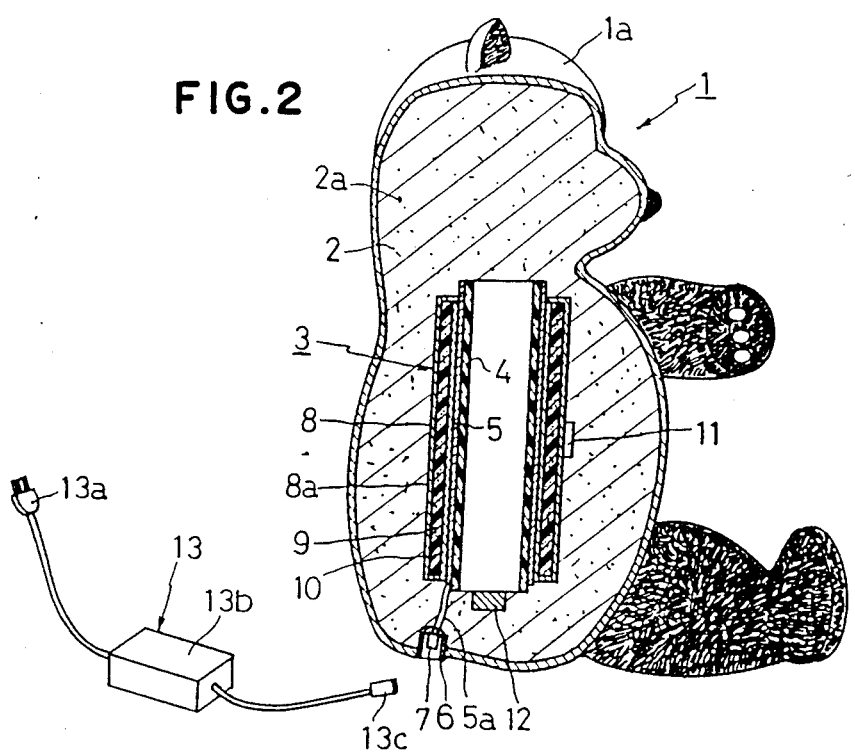
FIG. 2 is an elevational sectional view of the embodiment of FIG. 1 showing the latent heat storage unit and power supply.

One embodiment of the invention will now be described with reference to FIGS. 1 and 2.

Reference numeral 1 designates a stuffed animal toy, which includes a webbing or stuffing consisting of a heat insulation material 2a, e.g., urethane foam. The webbing 2 is covered by a cloth cover 1a having an outer shape like a panda.

A latent heat storage unit 3 is accommodated in the webbing 3. The unit 3 has a cylindrical core 4 made of polycarbonate. An electric resistor, i.e., a planar electric heater 5 of about 30 w., is provided around the outer periphery of the core 4, and its input terminal 5a is connected to a female connector 7 provided in an opening 6 formed in a rear bottom portion of the cover 1a.

The outer surface of the electric heater 5 is covered by a latent storage section 8, which consists of a synthetic resin film sack 8a and a non-woven cloth core 10 impregnated by about 200 g. of a latent heat storage material 9.

The latent heat storage material preferably comprises $NaCH_3COO.3H_2O$ as a main component and a nucleating agent comprising 90 to 10 weight % of anhydrous sodium acetate and 5 to 90 weight % of at least one of the other sodium salts selected from the group consisting of $Na_3PO_4$, $Na_2HPO_4$, $NaH_2PO_4$, $NaNH_4PO_4.4H_2O$, $Na_5P_3O_{10}$, $C_6H_5Na_2PO_4.2H_2O$, $NaBO_2.2H_2O$, $Na_2B_4O_7.10H_2O$, $Na_2C_2O_4$, $NaBr$, $NaCl$, $CH_2(COONa)_2.H_2O$, $(CHCOONa)_2.H_2O$, $(CH_2COONa)_2.6H_2O$, $HOC(CH_2)_2(COONa)_2.2H_2O$, $CH_3(CH_2)_2COONa$, $CH_3(CH_2)_6COONa$, $HOOCCH(NH_2)(CH_2)_2COONa.H_2O$ sodium oleate, and sodium stearate. This heat storage material is disclosed in U.S. Pat. No. 4,400,287 to Kimura et al., the substance of which is incorporated herein by reference.

Alternatively, the latent heat storage material 9 may comprise polyethylene glycol #6000, whose properties are as follows:

| | |
|---|---|
| Specific gravity 20/20° C. | 1.240–1.280 |
| Average specific heat in liquid phase cal/gr/°C. | 0.55 |
| Heat of fusion cal/gr | 46 |
| Surface tension 25° C. Dyne/cm | (d) |
| The heat of combustion 25° C. | 11.390 |
| Hygroscopicity (glycerol 100) | 1 |
| Vapor pressure (mm Hg 100° C.) | (e) |
| Flash point °F. | 520 (271° C.) |
| Appearance | white solid |
| Condition when dissolved in water (25) | transparent |
| Chromaticity (Pt. Co. color) | lower than 30 |
| Suspending material | none |
| PH (5% water solution at 25° C.) | 4.5–7.5 |
| Range of solidification point (°C.) | 56–61 |
| Viscosity (CKS-210° F.) | 700–900 |
| Ash (weight %) | lower than 0.02 |

In the above description (d) indicates being solid at a temperature of 25° C., and (e) indicates a value which is lower than $2.0 \times 10^{-12}$.

When the latent heat storage material 9 of the latent heat storage unit 8 is heated it undergoes a transition from the solid phase to the liquid phase, and it stores heat according to the heat of dissolution.

Further, when the material undergoes a transition from the liquid phase to the solid phase in use, it gives off heat according to the heat of solidification. The heat thus provided is utilized as the heater's heat.

Reference numeral 11 designates a thermostat. It is held in contact with the latent heat storage section 8. When the temperature of the latent heat storage section 8 exceeds a predetermined temperature, the thermostat produces a signal to operate a buzzer 12 secured to the underside of the core 4.

Reference numeral 13 designates an external power supply, which includes a plug 13a to be connected to an A.C. outlet of 100 v., a D.C. pack 13b and a male connector 13c.

To use the stuffed toy 1, the male connector 13c is connected to the female connector 7, and the plug 13a is connected to a power receptacle.

Figure 6:
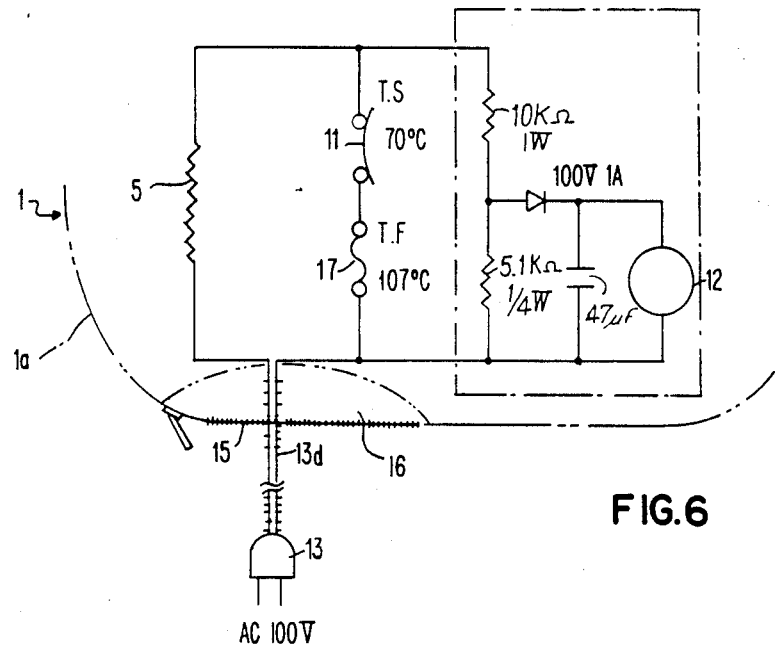
FIG. 6 is a wiring diagram of the heat storage unit shown in FIG. 5.

As shown in FIG. 6, in the case of heating it with the electric heater 5 by connection to an A.C. power source, it is convenient to provide a pocket 16 in the stuffed toy 1 which can open and close with a fastener 15, such as a zipper or the like, to accommodate a cord 13d having the plug 13a at its one end when the heating is finished.

The cord 13d with the plug 13a may be put into the stuffed toy 1 when heating the electric heater 5 from the A.C. power source.

When the electric heater 5 is energized for about 30 minutes to warm up the latent heat storage unit 3, the buzzer 12 operates to produce a sound indicating the completion of its heating. Then, the male connector 13c is disconnected, and the stuffed toy 1 is used in an embraced state or under a coverlet.

Figure 4:
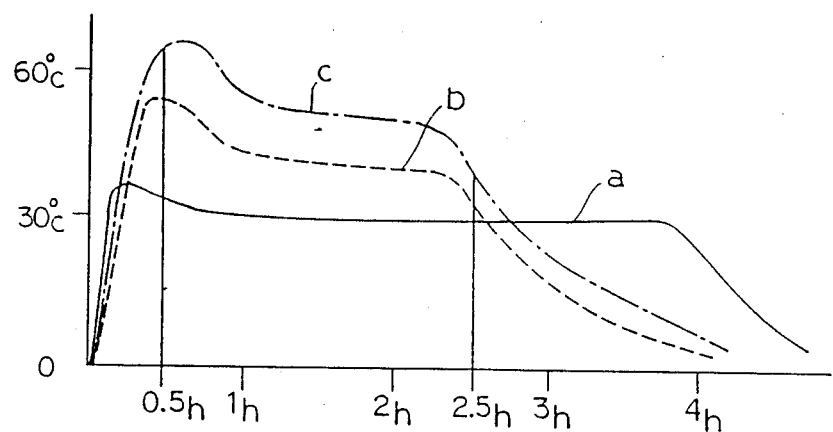
FIG. 4 is a graph showing temperature characteristics of a stuffed toy with heater according to the invention which uses polyethylene glycol #6000 as a latent heat storage material, and prior art stuffed toys with heaters.

A solid curve a in FIG. 4 shows the temperature of the cover surface of a stuffed toy according to the invention which uses polyethylene glycol #6000 as a latent heat storage material. Since heat is stored in the latent heat storage unit 3 by the electric heater 5, at the time of the heating the temperature slightly exceeds 30° C. Subsequently, the temperature is maintained at approximately 30° C. for about 4 hours.

Curve b in FIG. 4 indicates a prior art stuffed toy which has a comparatively inferior heat preservation property and curve c indicates a prior art stuffed toy which has a comparatively superior heat preservation property.

FIG. 7 shows the temperature characteristics of a stuffed toy according to the invention which uses as the latent heat storage material a compound selected from the group disclosed and claimed in U.S. Pat. No. 4,400,287 to Kimura et al. Curve A represents the temperature of the latent heat storage material 9 and curve B represents the temperature of the cover surface of a stuffed toy according to the invention. Point "S" indicates the time when the heater is again switched on.

When heating is complete, the temperature of the surface of the stuffed toy is approximately 58° C. As shown in FIG. 7, the temperature of the cover surface of the toy is maintained between 58° C. and 40° C. for approximately at least 5 hours. The temperature of said latent heat storage material is maintained substantially constant in the range of approximately 50° C.–55° C. for approximately at least 4 hours and the cover of said stuffed toy is maintained substantially constant in the range of approximately 40° C.–45° C. for approximately at least 4 hours.

The melting point of the latent heat storage material 9 whose temperature characteristics are shown in FIG. 7 is 55° C.±1.5° C. and the freezing or solidifying point is 52° C.±1.5° C.

The temperature of the latent heat storage material 9 in the liquid phase (i.e., the temperature of the flat portion of the curve) is suitably set such that the heat temperature of the surface of the stuffed toy 1 is close to the temperature of the animal whose shape is resembled by the shape of the toy.

It will be understood that the temperature characteristic noted above has less changes and a longer temperature preservation time compared to temperature characteristics of prior art stuffed toy structures.

Figure 3:
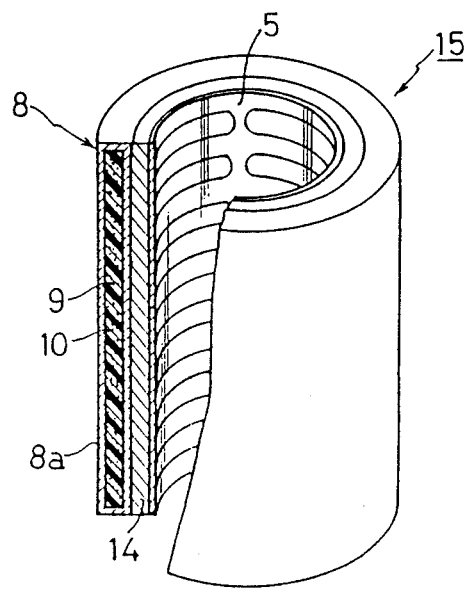
FIG. 3 is an enlarged-scale perspective view, partly broken away, showing a latent heat storage unit different from that shown in FIG. 2.

FIG. 3 shows a different embodiment of the latent heat storage unit according to the invention, which is designated generally by numeral 15. In the figure, like parts used in the preceding embodiment are designated by the same reference numerals.

In this instance, a heat dissipation member 14 made from an iron sheet is provided between the latent heat storage section 8 and the electric heater 5.

In this latent heat storage unit 15, heat from the electric heater 5 is dissipated so as to be transferred uniformly to the latent heat storage section 8, and all portions of the electric heater 5 are held at an equal temperature at all times.

While in the above embodiments the cloth core 10 impregnated with the latent heat storage material 9 is accommodated in the resin film sack 8a, it is also possible to fill an evacuated hollow metal cylinder with the latent heat storage material.

Furthermore, the heat dissipation member 14, may comprise an iron sheet or alternately a member consisting of a metal net of fine metal with wires or one consisting of a mass of aluminum or like foils.

Additionally, the stuffed toy may have a shape resembling a doll or a pillow as well as an animal.

In a further embodiment, it is possible to use a latent heat storage unit 3 which can be removably inserted into the stuffed toy after heat is stored outside the toy.

Figure 5:
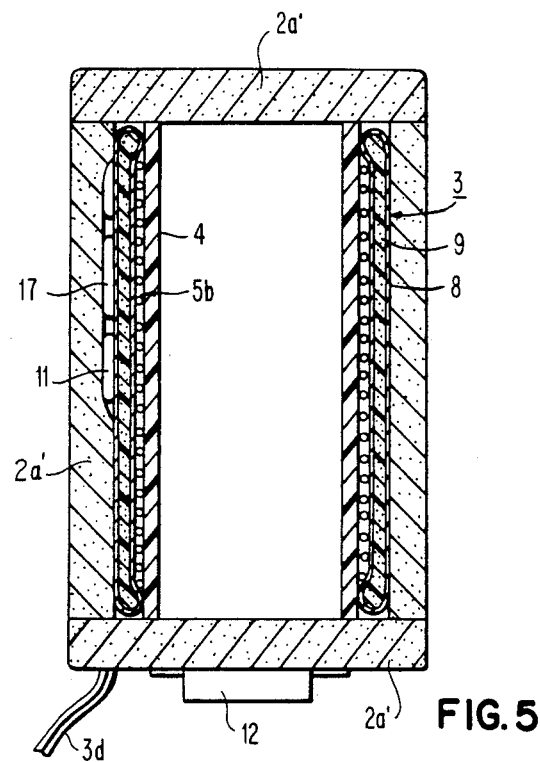
FIG. 5 is a longitudinal sectional view of a heat storage unit.

FIGS. 5 and 6 show an embodiment of the present invention wherein a heater 5b is constructed in a compact manner and which directly heats the latent heat storage material 9 through the latent heat storage section 8 by applying a conventional A.C. power source to said heater. At the periphery, the core 4 is wound up with a core shaped heater 5b which is coated with a coating made of silicone rubber at a predetermined pitch. The combination of the heater 5b and its coating is referred to herein as a "heater unit". The core shaped heater 5b is made so as to satisfy safety standards even if it is directly connected to the commercial A.C. power source.

In the present invention it is contemplated that the heater 5b is operative only in the period when heat is being accumulated in the latent heat storage material 9. The completion of heat accumulation is detected by the thermostat 11 when it detects a temperature of 70° C. The heater 5b is then disconnected from the A.C. power source and the buzzer 12 begins to sound to announce that the heat accumulation is complete.

In case of the thermostat 11 being inoperative or the heater being heated to extraordinarily high temperatures for some reason or other, a fuse 17 will melt to completely break the electric connection to assure safety. The outside of the latent heat storage unit 3 is covered with a warm material 2a' of a certain thickness. Of course, it is also possible to insert a heat dissipation member made of metallic material such as the iron sheet 14 described above or the like between the electric heater 5b and the latent heat storage material 9 directly or with any appropriate cover.

In this embodiment, since the heater 5b with its silicone rubber coating is made as a unit, any particular warm material 2a is unnecessary around the heater 5b itself. Any material can be used as webbing or stuffing material 2 of the stuffed toy 1. In addition, the heater unit of this embodiment is easily manufactured and advantageously meets applicable safety standards.

Since the heater 5b is heated directly by the AC power source, very high energy conversion efficiency at heat storage (accumulation) can be achieved. In addition, when the stuffed toy is used, a cord 3d is disconnected or removed, so that extreme safety toy.

As has been described in the foregoing, with the latent heat storage material used as a heater it is possible to reduce temperature changes when used, which is quite desirable from a health standpoint.

Furthermore, any temperature fall due to heat dissipation is small, and the toy can be continuously used for a long period of time.

The embodiments of the invention shown and disclosed herein are merely illustrative, as the invention is susceptible to variation, modification and change within the spirit and scope of the appended claims.

What is claimed is:

1. A stuffed toy for transferring heat to a user's body upon contact comprising a heat-transmitting cover configured to resemble a predetermined object and defining an enclosed cavity therein, a latent heat storage unit enclosed by heat insulating stuffing material disposed in said cavity, said stuffing material being covered by said cover, said latent heat storage unit comprising:
    core means;
    an electric heater disposed around an outer periphery of said core means; and
    a latent heat storage section substantially surrounding said electric heater, said latent heat storage section comprising impermeable flexible sack means having an outer wall and an inner wall and retaining therebetween a latent heat storage phase changable material, the inner wall of said sack means located adjacent said electric heater, said latent heat storage material for maintaining said stuffed toy at a substantially constant temperature for a period of approximately at least 5 hours, thereby imparting to a user contacting the outside surface of said cover a warm sensation which is maintained constant for said period.

2. The stuffed toy of claim 1 wherein said latent heat storage material comprises $NaCH_3COO.3H_2O$ as a main component and a nucleating agent comprising 90 to 10 weight % of anhydrous sodium acetate and 5 to 90 weight % of at least one of the other sodium salts selected from the group consisting of $Na_3PO_4$, $Na_2HPO_4$, $NaH_2PO_4$, $NaNH_4PO_4.4H_2O$, $Na_5P_3O_{10}$, $C_6H_5Na_2PO_4.2H_2O$, $NaBO_2.2H_2O$, $Na_2B_4O_7.10H_2O$, $Na_2C_2O_4$, NaBr, NaCl, $CH_2(COONa)_2.H_2O$, $(CHCOONa)_2.H_2O$, $(CH_2COONa)_2.6H_2O$, $HOC(CH_2)_2(COONa)_2.2H_2O$, $CH_3(CH_2)_2COONa$, $CH_3(CH_2)_6COONa$, $HOOCCH(NH_2)(CH_2)_2COONa.H_2O$ sodium oleate, and sodium stearate.

3. The stuffed toy of claim 1 wherein the temperature of said latent heat storage material is maintained substantially constant in the range of approximately 50° C.–55° C. for approximately at least 4 hours.

4. The stuffed toy of claim 1 wherein the cover of said stuffed toy is maintained substantially constant in the range of approximately 40° C.–45° C. for approximately at least 4 hours.

5. The stuffed toy of claim 1 wherein said cover comprises a layer of soft flexible heat transmitting fabric configured to resemble a decorative shape selected from the group consisting of stuffed animals, dolls or pillows.

6. The stuffed toy of claim 1 wherein the inner and outer walls of the sack means are each comprised of flexible synthetic resin film sealed together to retain the latent heat storage material therebetween.

7. The stuffed toy of claim 1 wherein said latent heat storage material is retained in said sack means by means of a cloth core impregnated with said latent heat storage material.

8. The stuffed toy of claim 1 wherein said heater is in the shape of the core means and is coated with silicone rubber.

9. The stuffed toy of claim 1 wherein said core means comprises polycarbonate.

10. The stuffed toy of claim 1 further including a heat dissipation member disposed between said electric heater and said latent heat storage section.

11. The stuffed toy of claim 7 wherein said heat dissipation member is selected from the group consisting of an iron sheet, metal wire net or metal foils.

12. The stuffed toy of claim 1 wherein said electric heater is connected to a power supply via a cord removably attached to said cover.

13. The stuffed toy of claim 1 wherein said electric heater is connected to a power supply via a cord capable of being accommodated in a pocket made in said cover.

14. The stuffed toy of claim 9 wherein a fuse is provided in a circuit of said electric heater to disconnect it from said power supply when the temperature of said latent heat storage unit reaches approximately 107° C.

15. The stuffed toy of claim 1 wherein a thermostat is provided in said latent heat storage unit so as to disconnect the power supply to said heater when a temperature above approximately 70° C. is detected.

16. A stuffed toy for transferring heat to a user's body upon contact comprising a heat-transmitting cover configured to resemble a predetermined object and defining an enclosed cavity therein, a latent heat storage unit enclosed by heat insulating stuffing material disposed in said cavity, said stuffing material being covered by said cover, said latent heat storage unit comprising:
    core means;
    an electric heater disposed around an outer periphery of said core means; and
    a latent heat storage section substantially surrounding said electric heater, said latent heat storage section comprising impermeable flexible sack means having an outer wall and an inner wall and retaining therebetween a latent heat storage phase changable material, the inner wall of said sack means located adjacent said electric heater, said latent heat storage material for maintaining said stuffed toy at a substantially constant temperature for a period of approximately 4 hours, thereby imparting to a user contacting the outside surface of said cover a warm sensation which is maintained constant for said period.

17. The stuffed toy of claim 16 wherein said latent heat storage material comprises polyethylene glycol #6000.

18. The stuffed toy of claim 16 wherein the cover of said stuffed toy is maintained substantially constant at approximately 30° C. for approximately 4 hours.

19. The stuffed toy of claim 16 wherein said cover comprises a layer of soft flexible heat transmitting fabric configured to resemble a decorative shape selected from the group consisting of stuffed animals, dolls or pillows.

20. The stuffed toy of claim 16 wherein the inner and outer walls of the sack means are each comprised of flexible synthetic resin film sealed together to retain the latent heat storage material therebetween.

21. The stuffed toy of claim 16 wherein said latent heat storage material is retained in said sack means by means of a cloth core impregnated with said latent heat storage material.

22. The stuffed toy of claim 16 wherein said heater is in the shape of the core means and is coated with silicone rubber.

23. The stuffed toy of claim 16 wherein said core means comprises polycarbonate.

24. The stuffed toy of claim 16 further including a heat dissipation member disposed between said electric heater and said latent heat storage section.

25. The stuffed toy of claim 24 wherein said heat dissipation member is selected from the group consisting of an iron sheet, metal wire net or metal foils.

26. The stuffed toy of claim 16 wherein said electric heater is connected to a power supply via a cord removably attached to said cover.

27. The stuffed toy of claim 16 wherein said electric heater is connected to a power supply via a cord capable of being accommodated in a pocket made in said cover.

* * * * *